(12) United States Patent
Vittorio (10) Patent No.: US 11,238,114 B2
(45) Date of Patent: *Feb. 1, 2022

(54) EDUCATIONAL CONTENT SEARCH AND RESULTS

(71) Applicant: Steven Michael Vittorio, Gainesville, FL (US)

(72) Inventor: Steven Michael Vittorio, Gainesville, FL (US)

( * ) Notice: Subject to any disclaimer, the term of this patent is extended or adjusted under 35 U.S.C. 154(b) by 333 days.

This patent is subject to a terminal disclaimer.

(21) Appl. No.: 14/521,110

(22) Filed: Oct. 22, 2014

(65) Prior Publication Data

US 2015/0111190 A1 Apr. 23, 2015

Related U.S. Application Data (60) Provisional application No. 61/894,378, filed on Oct. 22, 2013, provisional application No. 61/979,555, filed on Apr. 15, 2014.

(51) Int. Cl.
| | | |
|---|---|---|
| *G06F 16/9535* | (2019.01) | |
| *G09B 5/02* | (2006.01) | |
| *G09B 5/04* | (2006.01) | |
| *G06F 16/2457* | (2019.01) | |
| *G16B 50/50* | (2019.01) | |

(52) U.S. Cl.
CPC .... *G06F 16/9535* (2019.01); *G06F 16/24578* (2019.01); *G09B 5/02* (2013.01); *G09B 5/04* (2013.01); *G16B 50/50* (2019.02)

(58) Field of Classification Search
CPC .............. G06F 3/0488; G06F 16/9535; G06F 16/24578; G06F 19/324; G16B 50/50

USPC ......................................................... 434/322
See application file for complete search history.

(56) References Cited

U.S. PATENT DOCUMENTS

| | | | |
|---|---|---|---|
| 6,626,959 B1 | 9/2003 | Moise et al. | |
| 6,987,945 B2 | 1/2006 | Corn et al. | |
| 7,526,475 B1 | 4/2009 | Verstak et al. | |
| 8,001,141 B1 * | 8/2011 | Bar | G06Q 30/06 707/769 |
| 8,090,717 B1 * | 1/2012 | Bharat | G06F 16/355 707/731 |

(Continued)

FOREIGN PATENT DOCUMENTS

WO    WO-2014/071033 A1    5/2014

OTHER PUBLICATIONS

Final Office Action dated Nov. 18, 2019 in U.S. Appl. No. 15/030,817.

(Continued)

*Primary Examiner* — Thomas J Hong
*Assistant Examiner* — Sadaruz Zaman
(74) *Attorney, Agent, or Firm* — Saliwanchik, Lloyd & Eisenschenk (57) ABSTRACT

A search request for educational content can be initiated by a user, and the educational content that is relevant to the search request can be identified. The identified educational content can be ranked based on the number of times the content has been referenced as well as the university or other educational institution that referenced the educational content. The relevant identified educational content can then be displayed in an ordered list that is ordered based on the number of times the content has been assigned.

20 Claims, 7 Drawing Sheets

(56) References Cited

U.S. PATENT DOCUMENTS

| | | | |
|---|---|---|---|
| 8,352,467 B1 | 1/2013 | Guha | |
| 8,392,244 B1 | 3/2013 | O'Halloran | |
| 8,417,698 B2 | 4/2013 | Yoo | |
| 8,616,895 B2 | 12/2013 | Brown | |
| 8,676,828 B1 * | 3/2014 | Agarwal | G06F 17/2247 |
| | | | 705/14.4 |
| 8,805,814 B2 | 8/2014 | Zijlstra et al. | |
| 8,954,420 B1 * | 2/2015 | Khan | G06F 16/24578 |
| | | | 707/722 |
| 8,972,391 B1 | 3/2015 | McDonnell et al. | |
| 10,162,900 B1 * | 12/2018 | Chatterjee | G06F 16/248 |
| 2002/0078045 A1 | 6/2002 | Dutta | |
| 2002/0161757 A1 | 10/2002 | Mock et al. | |
| 2003/0040976 A1 | 2/2003 | Adler et al. | |
| 2003/0001448 A1 | 7/2003 | Goldmann et al. | |
| 2003/0125983 A1 | 7/2003 | Flack et al. | |
| 2004/0153343 A1 | 8/2004 | Gotlib et al. | |
| 2004/0162772 A1 | 8/2004 | Lewis | |
| 2005/0026131 A1 | 2/2005 | Elzinga et al. | |
| 2005/0060312 A1 * | 3/2005 | Curtiss | G06F 16/9535 |
| 2005/0065959 A1 | 3/2005 | Smith et al. | |
| 2005/0228593 A1 | 10/2005 | Jones | |
| 2006/0112085 A1 | 5/2006 | Zijlstra et al. | |
| 2007/0185864 A1 | 8/2007 | Budzik et al. | |
| 2007/0255805 A1 * | 11/2007 | Beams | G09B 7/00 |
| | | | 709/218 |
| 2008/0046286 A1 | 2/2008 | Halsted | |
| 2008/0208624 A1 | 8/2008 | Morita et al. | |
| 2008/0270451 A1 | 10/2008 | Thomsen et al. | |
| 2009/0106799 A1 | 4/2009 | Park et al. | |
| 2009/0138371 A1 | 5/2009 | McGee | |
| 2009/0182725 A1 | 7/2009 | Govani et al. | |
| 2009/0271379 A1 | 10/2009 | Bakalash et al. | |
| 2009/0281988 A1 * | 11/2009 | Yoo | G06Q 30/02 |
| 2010/0179828 A1 * | 7/2010 | Kelly | G06Q 50/24 |
| | | | 705/3 |
| 2010/0211564 A1 | 8/2010 | Cohen et al. | |
| 2010/0268552 A1 | 10/2010 | Schoenberg et al. | |
| 2010/0286993 A1 | 11/2010 | Lovelace | |
| 2011/0004588 A1 | 1/2011 | Leitersdorf et al. | |
| 2011/0010366 A1 | 1/2011 | Varshavshy et al. | |
| 2011/0055189 A1 * | 3/2011 | Effrat | G06F 17/3064 |
| | | | 707/706 |
| 2011/0144908 A1 | 6/2011 | Cheong | |
| 2011/0173225 A1 * | 7/2011 | Stahl | G06Q 50/20 |
| | | | 707/769 |
| 2011/0212430 A1 | 9/2011 | Smithmier et al. | |
| 2011/0246468 A1 | 10/2011 | Raines | |
| 2012/0005201 A1 | 1/2012 | Ebanks | |
| 2012/0066167 A1 | 3/2012 | Fokoue et al. | |
| 2012/0066256 A1 * | 3/2012 | Ramamurthi | G06F 16/951 |
| | | | 707/771 |
| 2012/0117088 A1 | 5/2012 | Kawakami et al. | |
| 2012/0129139 A1 | 5/2012 | Partovi | |
| 2012/0221442 A1 | 8/2012 | Olejniczak et al. | |
| 2012/0245952 A1 | 9/2012 | Halterman et al. | |
| 2012/0251993 A1 | 10/2012 | Chidambaran et al. | |
| 2013/0040275 A1 | 2/2013 | Gowda | |
| 2013/0095464 A1 * | 4/2013 | Ediger | G09B 5/125 |
| | | | 434/322 |
| 2013/0097144 A1 | 4/2013 | Siamwalla et al. | |
| 2013/0173639 A1 | 7/2013 | Chandra et al. | |
| 2013/0262142 A1 | 10/2013 | Sethumadhavan et al. | |
| 2013/0280682 A1 | 10/2013 | Levine et al. | |
| 2014/0006930 A1 * | 1/2014 | Hollis | G06F 17/2247 |
| | | | 715/234 |
| 2014/0058753 A1 | 2/2014 | Wild | |
| 2014/0108369 A1 * | 4/2014 | Nijjer | G06F 16/24578 |
| | | | 707/706 |
| 2014/0143232 A1 | 5/2014 | Abe | |
| 2015/0111190 A1 | 4/2015 | Vittorio | |
| 2015/0154646 A1 | 6/2015 | Mishra et al. | |
| 2015/0187228 A1 | 7/2015 | Boguski et al. | |
| 2015/0248484 A1 * | 9/2015 | Yu | G06F 17/30867 |
| | | | 707/711 |
| 2016/0111021 A1 | 4/2016 | Knoche et al. | |
| 2019/0325016 A1 * | 10/2019 | Nicholson | G06F 9/543 |

OTHER PUBLICATIONS

Office Action dated Jan. 1, 2021 in U.S. Appl. No. 15/566,977.
Office Action dated Apr. 6, 2020 in U.S. Appl. No. 15/566,977.
Office Action dated Sep. 4, 2020 in U.S. Appl. No. 15/030,817.
International Search Report in International Application No. PCT/US2014/061806, filed Oct. 22, 2014.
Office Action dated Apr. 27, 2018 in U.S. Appl. No. 14/521,149.
Notice of Allowance dated Dec. 18, 2018 in U.S. Appl. No. 14/521,149.
Office Action dated Nov. 2, 2017 in U.S. Appl. No. 14/521,149.
International Search Report in International Application No. PCT/US2016/028080, filed Apr. 18, 2016.

* cited by examiner

EDUCATIONAL CONTENT SEARCH AND RESULTS

CROSS-REFERENCE SECTION

This application claims the priority benefit of U.S. Provisional Application Ser. No. 61/894,378, filed Oct. 22, 2013, and U.S. Provisional Application Ser. No. 61/979,555, filed Apr. 15, 2014, both of which are incorporated herein by reference in their entirety.

BACKGROUND

Searching for educational content over the Internet can be difficult because it is not easy to determine whether a textbook or other educational content is the most appropriate for the task and topic at hand. Although there are a number of websites that sell or lend textbooks and other educational content, a search of this content is generally conducted directly using key terms input to a search bar.

Unfortunately, it is not always possible to determine which of a number of results would be the most likely one to be helpful in understanding a subject. Sometimes results are ranked according to relevancy, but the relevancy ranking may only be a function of a number of times a term is found in the text, or may be at least partly based off of user reviews, rankings, or responses. If the results are provided alphabetical or by release date, then there is no way to know which is the best book to read for a particular subject. In some cases, there may be reviews of the content, which can help inform the decision. However, the trustworthiness of the suggestion or review may be difficult to determine.

BRIEF SUMMARY

Systems and techniques for facilitating educational content search and results are described.

A search request for educational content can be initiated by a user, and the educational content that is relevant to the search request can be identified. The request may be via a search field or by navigating to a particular website directed to a topic or subject. The identified educational content can be ranked based on the number of times the content has been referenced. This ranking can further be influenced by the particular university, other educational institution, or library that referenced the educational content (for example, by assigning as required or recommended reading). The relevant identified educational content can then be displayed in an ordered list that is ordered based on the number of times the content has been referenced.

Educational content can be identified based on, for example, content title as well as the course names, course descriptions, degree titles, department names, and source names. For example, a search of "psychology" can include a search of book titles with the term "psychology" and course names, course descriptions, degree titles, department names, and college names that include the term "psychology." In some implementations, the search further involves a search of the text of the educational content. A database of related terms used to designate certain subjects can also be conferred to determine additional search terms related to "psychology," such as "behavioral science."

Relevant educational content can be made available for a user to access or purchase. In addition, the user can be informed of the referenced pages from each text.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Systems and techniques for facilitating educational content search and results are described. The educational content can be presented in a manner that indicates trustworthiness or relevancy based on an authoritative source—for example, a school, educational organization (private or government), or library. The content being referenced may include books, journal articles, website sources, course packet materials, video content, audio content, other multimedia content, software content, interactive demo content, transcriptions of spoken content into written content, and translations of content. It should be noted that, while books are frequently used as examples of educational content herein, the techniques and systems of the subject invention are applicable to a wide variety of educational content.

The sources referencing the educational content can include universities and other formal educational institutions such as preschool, primary school (elementary), secondary school (middle, junior high, high, community college), tertiary school (non-compulsory, university, undergraduate, graduate, post graduate, vocational), vocational school, and specialty school. Alternative education organizations and systems including, for example, homeschooling and self-learning systems as well as continuing education may also provide sources for educational content. Sources may also include libraries, such as school or university libraries, as well as other institutional libraries or research libraries.

A school or education organization may reference educational content by, for example, indicating particular content to be read, viewed, listened to, or otherwise used as part of an assignment; providing required, recommended, optional or suggested reading, viewing, and/or listening; or even listing the content as being authored or edited by an employee of the school. A library may reference educational content by possessing one or more copies of the content in the library's collection.

The manner that an educational content is referenced may in some implementations affect how the educational content is ranked and/or counted. For example, certain materials may be indicated as required reading for a class (e.g., specific pages are assigned as homework) whereas other materials may be suggested as supplemental, optional or additional reading (not specifically required as part of the homework assignment). In some implementations all or a subset of referenced materials are included as part of the results. In some implementations, only the required reading materials are included as part of the results. In other implementations, only the supplemental, non-required materials are included as part of the results. In some implementations, the manner in which educational content is referenced is indicated as metadata associated with the particular content.

In some cases, a weight may be assigned to the content (for the rankings) based on the manner in which educational content is referenced. In some cases, no distinction based on the manner in which the content is referenced is made in the rankings. In other cases, "assigned" (e.g., required as part of an assignment) may be weighted over "recommended" (e.g., not required/optional supplemental to an assignment) content. In yet other cases, a distinction may be provided between assigned material and recommended material through use of an indicator in the search results. Accordingly, it should be understood that the content ranking may be based on the manner in which content is referenced by a source (e.g., whether the manner falls into a category such as required, recommended, optional, extra/supplemental, and/or mentioned reading); and when reference is made to "referenced" content any combination of content found in a syllabus (or curriculum plan or other listing) for a particular course (or general subject) may be included in all permutations.

In some implementations, only "recommended" content is presented for a user. In some implementations only "required" (specifically assigned) content is presented for a user. In some implementations, both the recommended and the required content are presented to the user. In some implementations where both the recommended and the required content are presented to the user, the system may be agnostic about the manner in which the content is referenced and may present results in a manner as if there is no difference between content that is recommended and content that is required. In some implementations where both the recommended and the required content are presented to the user, the manner in which the content is referenced may not affect how the content is ranked, but can be indicated to the user so that the user knows whether the content was a required content or recommended content by a particular source. One manner of indicating the manner in which the content was referenced is to include a particular icon or indication in association with the indicator of the class, school, or other level of granularity relevant to the source that referenced the content. In some cases, faces of teachers/professors may be used.

In some implementations where both the recommended and the required content are presented to the user, the manner in which the content is referenced can affect the rankings. For example, each "required" reference to a piece of content may be weighted differently than each "recommended" reference to that piece of content. As another example, the number of required references to a piece of content may be used as a tie-breaker when two pieces of content have a same number of total references, but differing numbers of required references (e.g., both pieces of content have 10 references, but one was referenced as required 7 times and the other was indicated as required only 6 times—the remaining references being recommendations).

In some implementations, sections within referenced content can be ranked, where the referenced portions of each educational content result can be presented.

The information about educational content referenced by a school (or education organization) may be gathered from sources including, but not limited to, schools, professors, teachers, libraries, course syllabi, school websites, faculty, book stores (online and brick-and-mortar), library holdings catalogs, and even students (who relay the assignments, required, and recommended materials given by their school).

Figure 1:
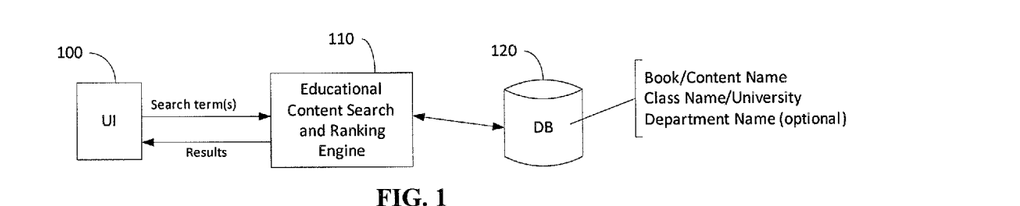
FIG. 1 illustrates an operating environment in which embodiments may be implemented.

FIG. 1 illustrates an operating environment in which embodiments may be implemented. Referring to FIG. 1, a user may conduct a search of educational content through a user interface (UI) 100. The search can be conducted on course titles, titles of content (e.g., book titles), text within the content, school (including department) and/or library, degree title, or a combination of one or more of these categories. The areas for the search may be specified by the educational content search and ranking engine 110 (e.g., via a drop-down menu) or may include free-form input provided by the user via the user interface 100 (e.g., via a search bar).

Figure 2:
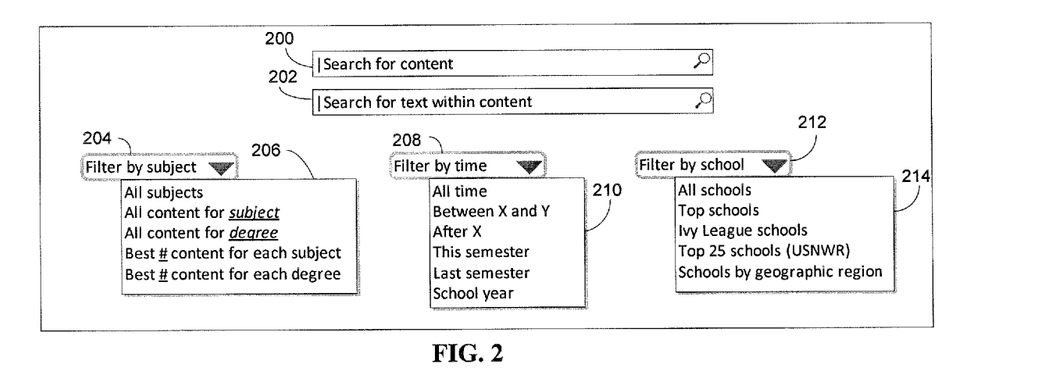
FIG. 2 illustrates an example user interface of a search page.

The user interface may include features as illustrated in FIG. 2. As shown in FIG. 2, a first input field 200 can be provided for receiving a search query for content. In some cases, a second search field 202 may be provided for searching for text within content. The search fields may be separate input fields or a single input field for conducting one or both searches. The search query may be refined by using one or more filters.

In some embodiments, when a search is conducted for text within content, the results can surface matching search terms as well as context for the matching search terms. For example, 80 words in front of and 80 words following a matching term in a piece of content can be displayed as part of the result for searching text within content. In some cases, the portions of the content that are shown first can be based on the amount of discussion related to the search query. For example, a matching word in a list may be given less prominence than sections of text containing substantive discussion related to the query. Also for example, a preview that would feature more matches of the search term(s) would be ranked above a preview that would contain fewer, and this may be a tie breaker for within content ranked previews.

In some embodiments, when a search is conducted for term(s) within content, the results can surface content (and corresponding previews when used) that contain a matching (or related) term both within the content and in meta-content, such as the prefix, index, glossary, summary, and table of contents. In some embodiments, only the pages listed from a specific table of contents, prefix, summary, or index match may be shown. In some embodiments, matches for content contained in the prefix, summary, index, glossary, or table of contents may be excluded from the results. In some embodiments, content related to the search terms may be required to be in the content and within the index, glossary, or table of contents, which may minimize the return of results that mention a term but do not relate to the appropriate topic/concept/subject. In some implementations, any matching content may be returned. Any and all content matching options may be user-selectable.

Users do not need to do a search to access the content as the content may be listed in a default or otherwise optimized manner before a specific search is entered by the user. In some implementations, an ordered listing of content can be presented on a landing page (e.g., "home page") of an educational content listing website rendered in a user's browser application (and providing a user interface to the educational content search and ranking engine). The default ordered listing may be of content for all the schools (as known from the database or other structured data stored on a resource for the educational content search and ranking engine).

For example, the schools included in "all the schools" may be through school ranking systems such as the U.S. News and World Report Best Education rankings (e.g., Best Colleges, Best Graduate Schools, Best Online Programs, Best High Schools, and the like). The home page may then show all the educational content for the top number of schools indicated by the ranking system in an ordered list of content according to the number of times that content is referenced by those schools (where, for example, each item of content is counted only once per school even where multiple courses at that school may reference the content). Specific tie-breakers may be applied to determine the order of the content when more than one item of content is referenced the same number of times. User-adjustable filters may be used to narrow the results before a search is conducted or after the search is conducted. Educational content may be, for example, books, videos, and articles.

A "filter by subject" 204 can provide filtering options 206 such as, but not limited to, enabling a search of content for all subjects, all content for a specified subject, all content for a specified degree, a designated number of content for each subject (e.g., "top 10 psychology books") and a number of content for each degree (e.g., "top 25 books for a degree in civil engineering") as some examples. Filtering by one or more topics may also be accomplished.

A "filter by time" 208 can provide filtering options 210 such as, but not limited to, enabling a search of content referenced at any time, between certain dates, after a certain date, for a certain year, for a certain school year, for the present semester, for a previous semester, and a designated one or more semesters as some examples.

A "filter by school" 212 can provide filtering options 214 such as, but not limited to, enabling a search of content for one, multiple, or all schools, for designated schools such as top schools, for Ivy League schools, for the top 25 (or other "top" number) schools according to the U.S. News and World Report rankings or other rankings, and schools by geographic region as some examples.

Other filter types are also possible. For example, searches may be filtered according to educational source in other ways, including but not limited to, magnet (and or charter) programs or schools, school districts, specialized schools, school board, school zone, and grade levels. Additional filter categories may be added to further filter results by type/kind/category of content, e.g., book, article, video, audio recording, multimedia contents, interactive demo, and training software.

In some embodiments, available filter options may be determined or dynamically redefined by prior filter selections, as for example when selection of a "degree" filter surfaces an additional filter based on different degree names. Sub-filters may, for example, further refine broader content types (e.g., novel and textbook as sub-types of book) or language (e.g. English, Spanish), or original language.

Of course other designations may be provided and even natural language queries may be used in certain implementations. The manner and menu for applying the filter(s) may be, for example, any suitable tool bar, input field or menu for providing the information.

A degree, class schedule, or interest search may be carried out through the described search and ranking engine via a content search 200. For example, in response to receiving a request for content directed to a degree program (set using filter element 204) and a time factor like a grade level (including continuing education) (set using filter element 208), the system can provide results of referenced content to cover the referenced content from the requested grade level (or age) through completion of the degree according to the available or selected educational sources.

In some implementations, a degree audit may be provided as a filter of the educational content. The degree audit search or filter may be used as an entry point to other searches, for example, each course for the degree can generate ordered listings of educational content. A keyword search may be used or a comparison of courses for degrees from a set of sources (e.g., a set of schools). The degree audit may incorporate class name filtering/search. For example, a degree audit may return content that school(s) reference for the particular class names corresponding to the degree. In some cases, the courses may include general education requirements as well as core curriculum. The results may be further filtered according to year (e.g., what the degree courses were for a particular year) and time-frame (e.g., from what grade level to what grade level). Searches may be conducted within the results in any manner such as described herein. In some cases, the exact course names for selected schools (or continuing education or professional education) (from the selected schools degree audits) are used to generate the results for the degree audit search and/or filter. In some cases, key words are used to generate results for the various courses expected for a degree.

It should be understood that the degrees (optionally including certification) available for the degree audit may include primary or secondary school level programming or curriculum as well as or in addition to college and university level curriculum, and professional level, including board requirements and certifications. In some cases, the degree audit can be based on published or official school curriculum. In some cases, the degree audit can be based on what students actually took to obtain their degree (or attain graduation to a next level). Electives and minors may be included. In yet other cases, a combination of official school curriculum and student-reported courses may be used.

Results of degree audits may include highlighting or other indications emphasizing particular content. For example, a top 10 content may be indicated covering a top content for each of 10 courses (or less courses and more content associated with the courses) so that a user may obtain a cohesive picture for the degree and possibly be inclined to view and/or purchase the content. As one example, a top 20 items for a law degree may be presented to the user; each item being a most referenced for a particular course. The highlighting may guide a user to specific subjects within the general subject of law.

In some cases, results of a degree audit may be organized by specific degree or subject name or by a more general topic name (e.g., specific degree of tax law or more general topic of law; a specific degree of cognitive psychology or a more general topic of psychology).

Degree audits may include any of the filtering described herein (e.g., subject, time, school, within content). Filtering by school(s) can facilitate a comparison of degree/major audits across schools. Other filters may be available, including filtering by degree, which may use same named degrees across schools along with their respective degree audits with listed class names to search all listed class names and the degree name itself, in order to return a filtered ranked list by degree. In some cases, filtering by subject may filter by class name(s) (or major or major/degree) and may be used in place of or in addition to filtering by degree. A menu may be presented so a user can select a degree and then one or more subjects. It may also be possible to filter by teacher/professor or by ranking of teachers/professors (as indicated by review sites).

Returning to FIG. 1, search terms entered via the user interface (UI) 100 are used by an educational content search and ranking engine 110 to search a database (DB) 120. The database 120 can include structured information regarding educational content. A wide variety of educational content information may be stored, some of which may support the use of filtering categories described above. The database can be generated, for example, based on the books and other content referenced by universities. Elementary and secondary education may also provide syllabi (or other course or curriculum plans) that can be used to generate rankings.

The educational content search and ranking engine 110 can use the search terms provided via the user interface 110 to identify relevant educational content from the database 120. According to certain embodiments, the relevant educational content can initially be based on a search of content title (e.g., book name) and class name (e.g., for each university). In one such implementation, all books or other content titles that have matching terms in the class names are retrieved from the database and ordered/ranked. For example, when a course name matches a query (or a selected subject), then all the content referenced for that course is retrieved for inclusion in the list. All books or other content with titles matching the query (or the selected subject) can be retrieved for inclusion in the list.

In some cases, the relationship of search terms to meta-content, including for example in an "about" section, "summary" section, "introduction" section, "forward" section, "abstract" section and the like, may be used to determine whether a book or other content should be retrieved and ordered/ranked. In some embodiments, matches for content contained in, for example, the prefix, index, glossary, and/or table of contents may excluded from the results. In some embodiments, content related to the search terms may be required to be in the content and within the index, glossary, or table of contents, which may minimize the return of results that mention a term but do not relate to the appropriate topic. In some implementations, any matching content may be returned. These content matching options may be user-selectable.

In some cases, search terms may be iteratively altered to further refine search results. For example, if a search term returns results that overwhelmingly pertain to one type or subtype of content (e.g., a search term returns twenty results from "Law" degree content and only one from "Psychology" degree content), the search terms may be altered by the educational content search and ranking engine 110 to adjust the terms to be more directed toward a different content type or subtype.

The identified educational content can be ranked by the educational content search and ranking engine 110 based on the number of times the content has been referenced. The university or other educational institution that referenced the educational content may also influence the rankings (through filtering and/or weighting the number). In some implementations, the number of references to a particular educational content item may be counted per university, per class name, and per department, for example. In some implementations, the number may also be tabulated according to class terms, for example, per year, per semester, per quarter, and per course module.

The relevant identified educational content can then be displayed at the user interface 100 in an ordered list that is ordered based on the number of times the content has been referenced. In some cases, an indication of the number of times the content has been referenced can be provided.

In one embodiment, an initial search query may not be through the UI 100 and, instead, is a result of the request from a web browser to return information from a website (providing the UI 100) at a particular uniform resource location (URL). For example, when a user enters a URL in their web browser to go to the website specifically covering the topic of psychology, the hypertext language protocol (HTTP) request for the URL can initiate a query (e.g., based on a default search query in the string or as a field of the request) by the search and ranking engine 110 and those results can be rendered in the web browser as a default result list that can be part of the UI 100 before a user enters a specific query.

Figure 3A:
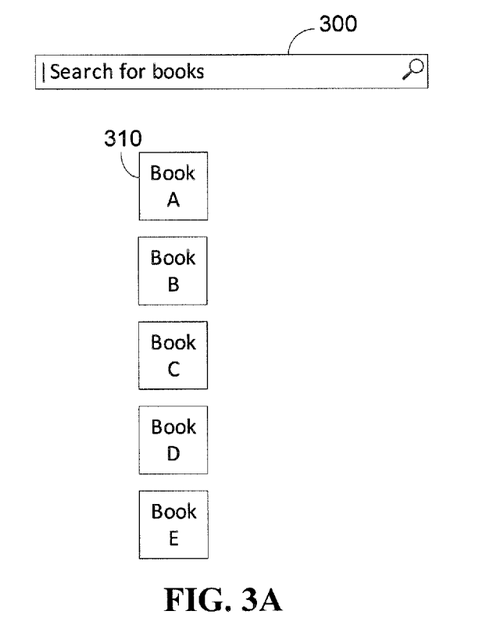
FIGS. 3A-3E illustrate example search result ordered list presentations.
Figure 3B:
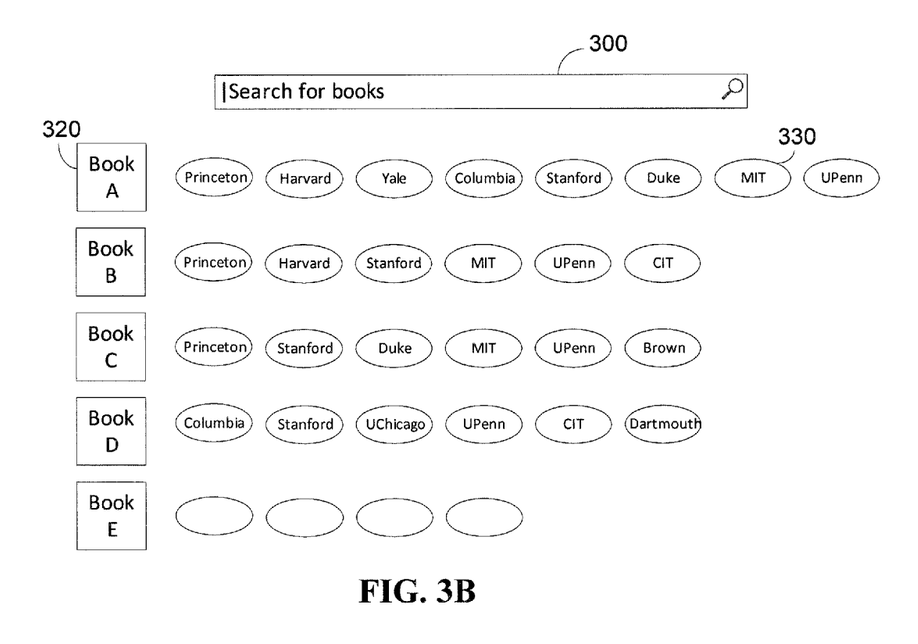

FIGS. 3A and 3B illustrate example search result ordered list presentations. Books are used as exemplary educational content in FIGS. 3A-3B, but should not be considered as limiting. In response to receiving a search query in the search input field 300 of a user interface, an ordered listing of books can be displayed. In FIG. 3A, the books 310 may be presented in a list from most referenced to least referenced. Additional filters (such as shown in FIG. 2) may be applied to further narrow the listing. Results of the search can be presented with indicators of the number of schools that referenced the book, a specific indicator (e.g., a badge or icon) for each school that references the book, the department names, each class to which the book was referenced and the corresponding school the class was in, and other information that can support the ranking of the book (e.g., provide information regarding the relevancy) and/or provide additional information that a user may use to select a text or obtain additional information.

For example, referring to FIG. 3B, the books 320 may be presented with an indicator 330 of the schools that referenced the book. In one implementation using an indicator (e.g., icon or badge) for a particular school that referenced a book, the indicator may be used only once per book even if the book is referenced by multiple courses at the school. Thus, each indicator represents that a school has referenced the book at least once. In another implementation, the indicator for a particular school that referenced a book may be used to represent each reference of the book so that multiple indicators for that particular school may be shown for the referenced book when multiple courses at that school reference the book. In another implementation, a counter may be displayed on the school indicator to indicate the number of times the book was referenced.

As mentioned above, results can be filtered. In one scenario, the results are filtered by school or a select grouping of schools. For example, the results can be filtered to show rankings based on Ivy League schools, by schools in a particular geographical region, by user-specified school or schools, by a top number of schools (as ranked by a school ranking system), or other school-related configuration.

As illustrated in FIG. 3B, each book includes an indicator of the university referencing the book. The indicators can be presented in order of the university's ranking on the U.S. News and World Report, or other university ranking system. Of course, it is contemplated that educational content from systems other than universities may be presented in addition to or in place of university-referenced content and that other schools may reference similar content as universities. Rankings for those schools and related organizations may be used in a similar manner as university rankings.

Within the results, when multiple content (e.g., books, articles, videos) in the results have a same number of sources that reference the content, the content having a same number of sources may be presented in alphabetical order. In some cases, the ranking order of tied results may be presented based on a ranking system of the schools that reference the content, such as the U.S. News and World Report. Of course, other university (and other school) ranking systems may be used. As an illustrative example, the results can be first ranked by grouping together books according to the percentage of schools that have referenced the book. Then, for ties within the same ranked books, the books that have a book title that matches key word(s) of the search may be presented first or the books that have the most class name matches to the key word(s) of the search may be presented first.

"Most class name matches" may be determined multiple ways. For example, every school with at least one class name match could count once and only once; then a ranking can be made between the schools to generate a school's class ranking within a named class ranking. As another example, across the board class name matches can be counted for the book as looked at across all schools referencing it. As yet another example, duplicate class names within a school would only count once. Of course, other tie breakers may be used.

Further ties may be broken by, for example, the average U.S. News and World Report rankings of the schools referencing the book, and ties still there may be broken by the highest ranked individual school of the tied books, and ties still there can be broken by the ABC order of the book titles.

Other non-limiting examples of tie-breaking methods include incorporating user reviews or ratings of content (where content have a 5 out of 5 star rating would be listed before content having a 4 out of 5 star rating).

In some scenarios, when multiple books have a same number of sources referencing the book, then these books can be ranked according to title first (e.g., percentage of key word(s) found in the title), and then by text within each book (the percentage of key word(s) or the number of times a term or topic is found within the textbook or within pages of the textbook that have been referenced). Books may also be ranked based on class/course name. For example, a school may have different courses that reference a same book. The search results can return books that are referenced to class names that are associated with the keywords of the search. If ten books are referenced by 5 schools each, these ten books can be ranked in alphabetical order of book title. In some cases, the books can be ranked by a combination of most relevant book titles and most relevant course titles (to the keyword(s) of the search), book title only, or course title only.

In addition, one or more tie-breaking methods may be applied to the listings of the results where a first tie breaking method does not break all the ties. As a non-limiting illustrative example, for ties within the same ranked books, the books that have a book title that matches key word(s) of the search may be presented first. Then, for the books that are tied for a same position, the books that have the most class name matches to the key word(s) of the search may be presented first. The books that have the most associated class name matches to the key word(s) may determine the next ordering both within the matched book title group and outside of the matched book titles group. Ties within these groups may next be broken by averaging the U.S. News and World Report rankings of the schools that referenced the books; higher averages can be listed before those with lower averages. For remaining ties, the highest ranked school that referenced the books can be used to order the books. Then, if there still remains a tie, the ABC order of book title may be used.

However, indicators may show other ranking criteria for educational content. For example, professor name, class name, major, minor, degree, and department indicators may be shown in some cases, depending on the criteria for ranking. In some cases, more than one type of indicator may be shown, and the indicators may be grouped by type. Groups of badges may include, for example, groups for the schools, professors, and classes using the content.

Figure 3C:
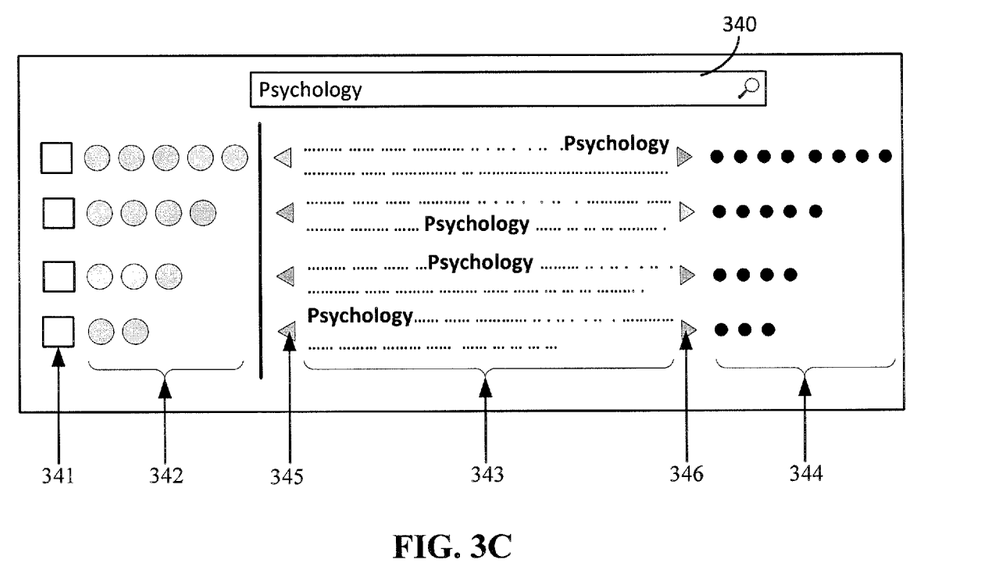

FIG. 3C shows an example ordered search result list presentation that may be used in some implementations. An interface is shown in FIG. 3C that contains both ranking information and the ability to navigate the textual content. The results for an example search of content related to "psychology" 340 are shown. A line in the result list shows a particular piece of educational content, such as a book or article. An area for depicting a visual icon of the content 341 may be available, as are ranking indicators 342. Reflecting the fact that ranking indicators 342 may be of multiple types and groupings, as discussed, the ranking indicators 342 are shown here without specific content, unlike as in FIG. 3B.

Textual content 343 may also be navigated within the search result presentation. One or more page locations, depicted by locator icons 344, may be shown. In the Figure, locator icons 344 show pages in the educational content having the search term "psychology." Selecting a locator icon may navigate the textual content 343 interface to the location in the content having the search term. Here, the textual content 343 interface shows "psychology" and a number of words in the text around the term. Navigation arrows (345, 346) may be available to move forward and backward within the text.

Figure 3D:
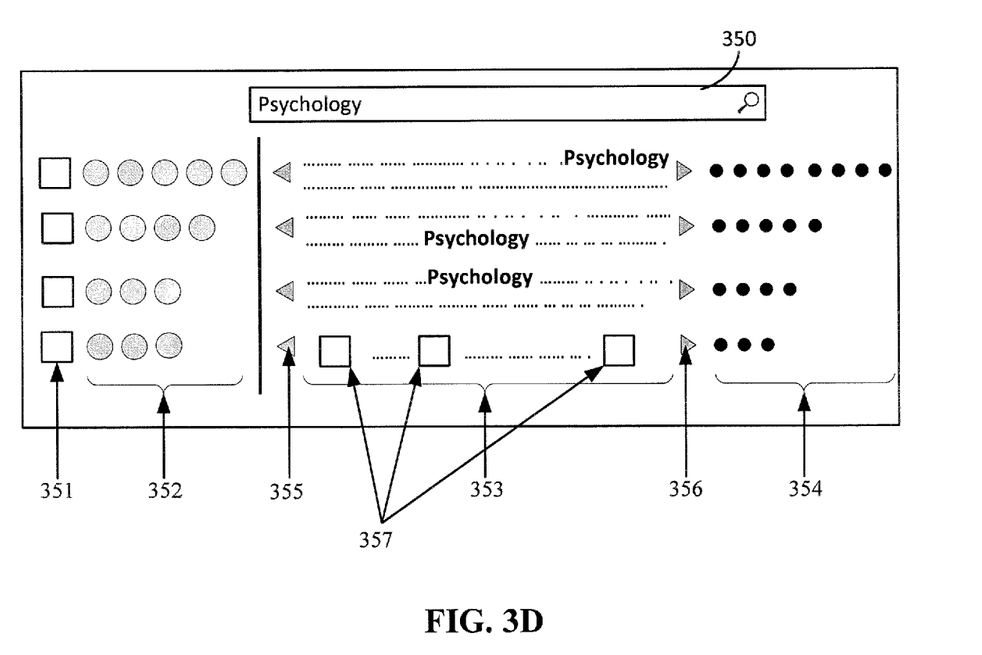

FIG. 3D shows a variation on the interface of FIG. 3C, where textual content is replaced by audio or audiovisual content. In FIG. 3D, one of the returned educational content results is a video. Familiar elements such as an icon 351, indicator badges 352, content review area 353, locator icons 354, and backward and forward arrows (355, 356) are shown, as in FIG. 3C. However, in the video content review area 353 for the video content, video clip segments are depicted using clip segment indicators 357. The clip segment indicators 357 may enable easier navigation to review the assigned time segments for a video type of educational content. As the interface in FIG. 3D shows, it is possible to navigate mixed content types in an example interface having these characteristics.

In some situations, it may be desirable for a user interacting with the user interface 100 to select individual items of content from a listing of search results so that several content options may be narrowed, compared, or searched further. The additional selections of content may form a user-created list of results that may then be searched and/or ranked further. For example, if a search of "psychology" returns a listing of content from several classes that include "psychology" in the title, only some of the content may be relevant to the user if the user only wants basic psychology content. The user may select the content that seems to fit his or her desired content. In some embodiments, the user's selection of content may form the basis for a user-defined result list that displays ranking information with respect to only the user's selected content. Some embodiments may enable additional searches by the user with respect to only the selected content. Some embodiments may allow the user to execute a function to find additional content using the selected content as a model for the search and ranking engine.

Figure 3E:
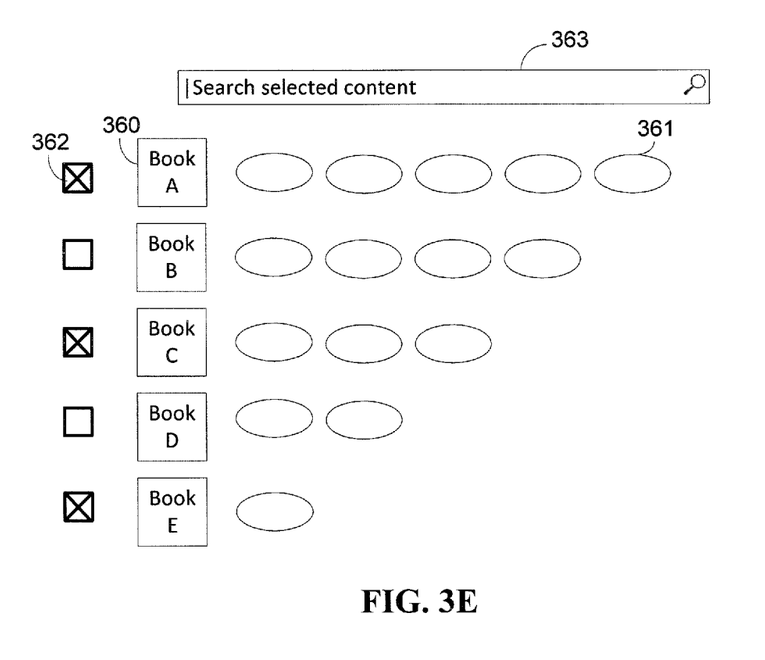

FIG. 3E shows an example of an embodiment that allows further selection of search results. In FIG. 3E, educational content 360, which may in some embodiments include ranking indicators 361, may be individually selected from the search results using additional interface elements. Checkboxes 362 are shown as examples of interface elements that may allow selection, but various kinds of interface elements may be used, as practitioners will appreciate. Selection of the results by the user may allow the user to create a secondary list that may then be ranked against one another using the described techniques. Additional interface options, such as a search box 363, may also be available to run searches against only the selected content items.

Figure 4:
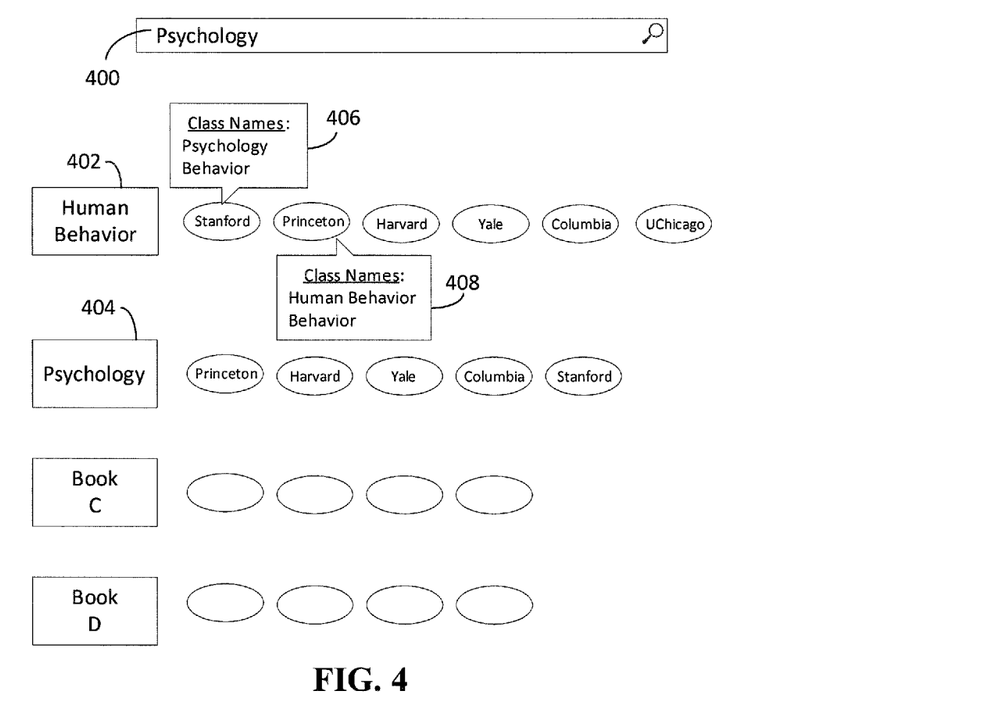
FIG. 4 illustrates an example search result.

FIG. 4 illustrates an example search result for a search of "psychology." For example, a user may enter "psychology" as the search query. The system then searches the database (or other structure such as a table) for books associated with "psychology." From the books associated with psychology, the most referenced books associated with a set of sources, for example 50 schools, can be presented in order from highest number of references to lowest number of references. The results can include a book titled "Human Behavior" 402 and a book titled "Psychology" 404. In the illustrated example, school indicators are included to show the universities that assign or recommend the book. For the book "Human Behavior," Stanford, Princeton, Harvard, Yale, Columbia, and the University of Chicago have all referenced the book.

In this FIG. 4 example, class titles are searched first, and then book titles. Other implementations may take a different order. The book "Human Behavior" is identified (along with other content) from a search of class titles with the term "psychology" because Stanford includes a class name of "Psychology" 406. Indicator popups (406, 408) may show additional information about the selection criteria for an indicator ranking, for example, by showing the class names for which the educational content was chosen. In the Figure, for example, the indicator for Stanford is shown before the indicator for Princeton even though Princeton ranks higher on the U.S. News and World Report ranking because one of Stanford's class names matches the search term, whereas Princeton's class names 408 for classes that reference the text book "Human Behavior" do not include the word "psychology."

Other information may be displayed in indicator popups 406 and 408. For example, indicator popups 406 and 408 may show professor names, professor rating metrics or scores, class names, educational source names, department information, major information, degree information, minor information, page citation counts, or other information that may be used to understand the basis for ranking indicators. The content in indicator popups 406 and 408 will, of course, vary by the nature and type of indicator used shown in the results presentation.

Figure 5:
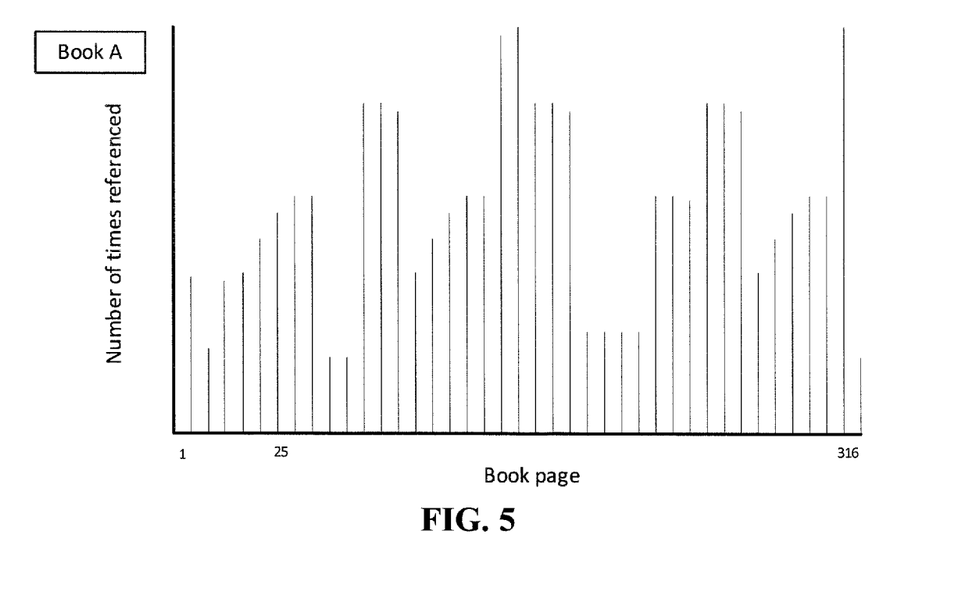
FIG. 5 illustrates an example user interface including a page graph.

FIG. 5 illustrates an example user interface including a page graph. In some implementations, additional information about referenced sections/chapters/pages of the text can be presented. FIG. 5 shows one manner of presenting information about the referenced pages, where a plot illustrates the number of times a page is referenced as part of the reading for a class (and across all classes or selected classes referencing the book). In some implementations, an independent page number on the graph can only go up/increase in relevancy in regard to being referenced, once per school, so as to make identical page references from a single school only count once while allowing different page references from classes within the same school to count. Then, when a separate school also references the page that has already been increased on the graph, the graph increases in relation to that page number of the book. In another implementation, the graphed page number(s) go up every time a non-identical class name within an independent school references the page(s). Different schools with a same named class are each counted, which allows for identical class names from separate schools to increase the page count on the graph.

In some implementations, a page graph may depict timing ranges in a video, audio, or other recording. The graph could show minutes or seconds rather than pages, if minutes are relevant to the content type. For example, if a class is assigned to watch a particular range of minutes in a particular video, the ranking would be increased for each class referencing the minute range. The count might be visually depicted using a graph similar to the page graph, but showing minutes or seconds instead of page numbers.

In some implementations, a page graph like the example shown in FIG. 5 may be presented in conjunction with other user interface elements so that page graph information may be compared between educational content. For example, a page graph may be displayed as an interface element of FIG. 3C for each returned educational content.

Figure 6:
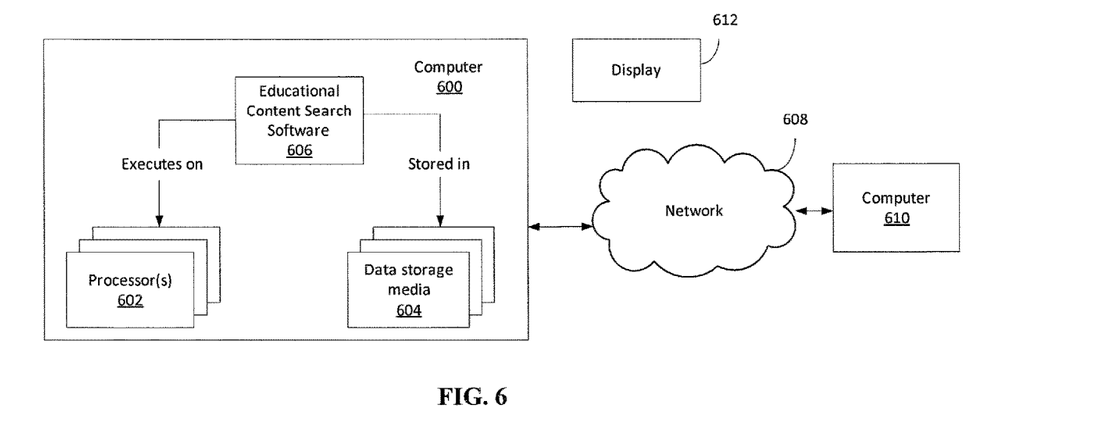
FIG. 6 is a block diagram of example components that may be used in connection with implementations of the subject matter described herein.

FIG. 6 shows an example environment in which aspects of the subject matter described herein may be deployed.

Computer 600 includes one or more processors 602 and one or more data storage media 604. Processor(s) 602 are typically microprocessors, such as those found in a personal desktop or laptop computer, smartphone, tablet, server, handheld computer, or other kind of computing device. Data storage media 604 are components that are capable of storing data for either the short or long term. Examples of data storage media 604 include, but are not limited to, hard disks, removable disks (including optical and magnetic disks), volatile and non-volatile random-access memory (RAM), read-only memory (ROM), flash memory, magnetic tape, and the like. The data storage media may also include other computer-readable storage media; however it should be understood that the data storage media and computer-readable storage media do not include propagating signals and carrier waves.

The computer 600 may include, or be associated with, display 612, which may be a cathode ray tube (CRT) monitor, a liquid crystal display (LCD) monitor, or any other type of monitor or display device.

Software may be stored in the data storage media 604. The software can be executed by the one or more processor(s) 602. An example of such software is educational content search software 606, which may implement some or all of the functionality described herein, although any type of software could be used. Software 606 may be implemented, for example, through one or more components, which may be components in a distributed system, separate files, separate functions, separate objects, separate lines of code, etc.

A computer (e.g., personal computer, server computer, handheld computer, smartphone, tablet) in which a program is stored on hard disk (or solid state drive or other storage media), loaded into RAM, and executed on the computer's processor(s) typifies the scenario depicted in FIG. 6, although the subject matter described herein is not limited to this example.

The subject matter described herein can be implemented as software that is stored in one or more of the data storage media 604 (or computer-readable storage media) and that executes on one or more of the processor(s) 602. The instructions to perform the acts could be stored on one medium, or could be spread out across plural media, so that the instructions might appear collectively on the one or more computer-readable storage media, regardless of whether all of the instructions happen to be on the same medium. It is noted that there is a distinction between media on which signals are "stored" (which may be referred to as "storage media"), and—in contradistinction—media that contain or transmit propagating signals. DVDs, flash memory, magnetic disks, etc., are examples of storage media. On the other hand, wires or fibers on which signals exist ephemerally are examples of transitory signal media. Thus, it will be understood that a storage media is non-transitory.

Additionally, any acts described herein (whether or not shown in a diagram) may be performed by a processor (e.g., one or more of processors 602) as part of a method. Thus, if the acts A, B, and C are described herein, then a method may be performed that comprises the acts of A, B, and C. Moreover, if the acts of A, B, and C are described herein, then a method may be performed that comprises using a processor to perform the acts of A, B, and C. In one example environment, computer 600 may be communicatively connected to one or more other devices through network 608. Computer 610, which may be similar in structure to computer 600, is an example of a device that can be connected to computer 600, although other types of devices may also be so connected.

Figure 7:
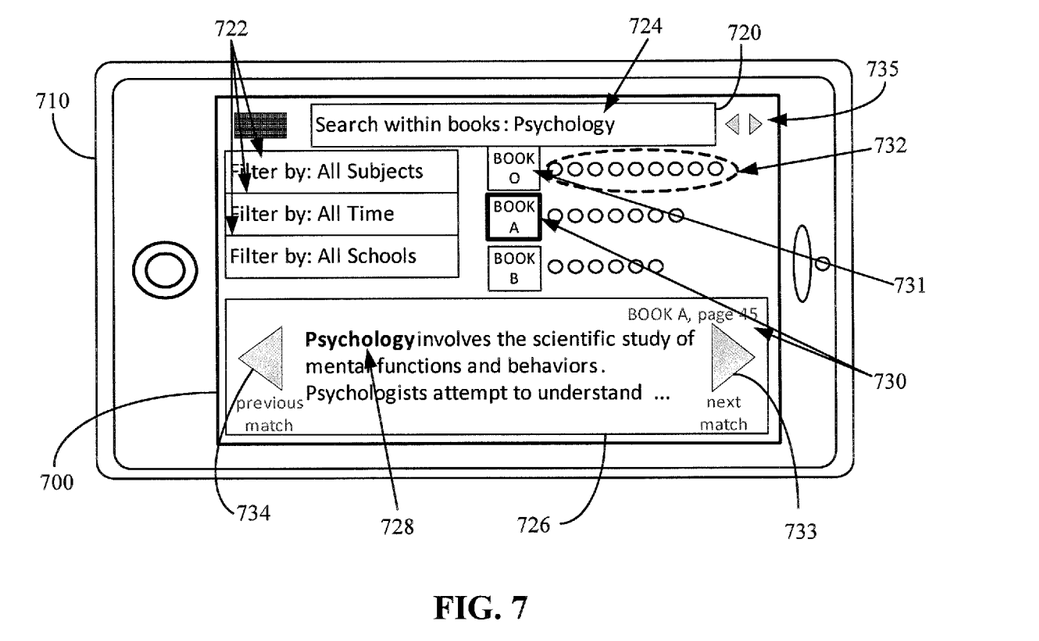
FIG. 7 illustrates an implementation of a user interface for small form factor devices.

FIG. 7 illustrates an implementation of a user interface for small form factor devices. Referring to FIG. 7, a user interface (UI) 700 for the educational search and ranking engine is shown that is suitable for a touch screen device 710, such as a smart phone. The UI 700 may include a search bar 720 and optional filters 722. Although three filters 722 are shown, these filters are presented for illustration and are not meant to be limiting in types (what is being filtered) or in number of available filters. In the example shown in FIG. 7, a query to search within books for "Psychology" 724 has been entered into the search bar 720. This screen may be in a state after a search for matching word(s) within a book has been conducted. A previous screen may be a home page that includes an ordered ranked list of all available content or a subject-specific (e.g., the subject of "Psychology") screen with a listing of content related to that subject. Of course, the page shown in the figure may be the originating screen.

In some cases, when searching within books, the UI 700 can include a preview 726 of the book(s) providing relevant text. For example, the matching term "Psychology" 728 from Book A (730) may be indicated along with a portion of the text around the matching term to provide context before a user selects to view the book 730, access more information about the book, or view another section either within Book A 730 or another book containing a matching term. In the example shown, a listing of books is also shown on the same screen as the preview 726. Here, three books, ranked according to any of the techniques described herein, are shown. Book O 731 has the most references (indicated by icons 732 representing the schools referencing the content), followed by Book A 730. After the user conducts a within-the-book search, the within content word match(es) with the highest ranking may be shown. The user may navigate through the content by selecting a next match 733 or previous match 734 for the preview 726 and/or by selecting a book from the ranked listing of books (either directly by selecting on the book icon or by indicating a next or previous (735) book.

Certain aspects may be made suitable for small form factors such as available through smartphones. In some embodiments for either within book search for matching words or a search for content in general, a school icon or indicator may be omitted or represented in a different manner. For example, a link can be provided instead of a set of icons so that a user can select the link to see the schools and/or classes that reference the content. As another example that may be used in addition to or as an alternative to the link, a number, ratio or percentage can be provided adjacent the book title (or book location) to indicate number of times the content is referenced (and provide a rank).

Certain aspects may be included that are suitable for large form factors. For example, large displays or projector screens may enable multiple results listings and previews. In addition, side-by-side views can be provided in a user interface to enable independent searching, filtering and/or types of results within a same view screen. In some cases, multiple types of searches (e.g., educational content searches, web search engines like GOOGLE and BING, video/audio content searches like available through YOU-TUBE, and specific database searches) can be performed and presented simultaneously in a side-by-side arrangement. In some cases, the multi-type search can involve a universal query (e.g., a same query or terms and/or filtering applied to all search types being presented) and specific search query functionality associated directly with each search type. In this manner, various levels of granularity of searching may be applied.

In FIG. 7, and in all content embodiments or within content preview embodiments and the like, there can be arrows that traverse to next or previous page, arrows for traversing to next or previous ranked page, and arrows for traversing by matches of the content based on page rank of matches (in some embodiments, navigation may start at the top of a page when there are multiple matches on same page or preview) and arrows for traversing by matches of the content front to back. In some embodiments, arrows may not be required and changing preview may be navigable like pages in a book, or traversed by rank of pages regardless if there is a match or not. Some implementations could have arrows that allow for next or previous page or traverse pages based on rank of page regardless of if there is a match on the page, or implementations wherein both can have arrows for both methods of traversing represented simultaneously.

The systems described herein may be carried out in a manner that facilitates free (from a user perspective) consumption of the educational content. In some implementations, a search within text of a book or other educational content can be provided for free to users by paying the content provider(s) (e.g., the copyright owner or publisher) a percentage of the ad revenue that is derived from advertisements shown when a user "opens" the book via the search within a book. The position/ranking of the book or other content on the list may also affect the payment. In addition, the type of content (e.g., video, book, article) may affect cost. Other considerations that can affect cost include the popularity of a piece of content, whether a specific piece of content is selected by an advertiser or a grouping of content is selected, and length of advertisement.

A user may be able to traverse text through a command indicating a request to view a next relevant location, for example by clicking on a button (e.g., via touch or mouse) or by voicing a command that brings the user to a next or previous place in the book that matches the search or to the next or previous most referenced book that has the text match within the text of the book, which will enable the user to search within the text of all books for free. The user can be presented with only the page on which the text matches as well as the page before and after the matching page. In another case, the user may access the text of a book for a period of time, for example 30 minutes, before the user is presented with another ad. Another advertisement may be shown at each 30 minute interval. The cycle may begin again for each book (or other content) that the user views. Alternatively, the advertisement interval may be per user time, resulting in the user being able to view any content and receiving an ad every 30 minutes regardless of the particular piece of content that the user is viewing. Time spent viewing a particular piece of content can still be tracked to facilitate the determination of the amount being paid to a content provider for access to the content.

In another case, the user may access the text of a book until a specified number of pages have been viewed. Then, the user would be presented with another advertisement if they want to keep reading within the text, and the cycle may be repeated. When a user "opens" another book, a new ad can be run, allowing the user to view a specified number of pages before another advertisement is shown. Alternatively, a user may be given a set number of pages that they may access after viewing an advertisement so that they may view any number of books (or other content) until the set number of pages (regardless of being different books or content) have been viewed. Pages viewed at a particular piece of content can still be tracked to facilitate the determination of the amount being paid to the content provider for access to the content.

Advertisements may be of different lengths and types. In some cases, the first advertisement to which a user is exposed may be shorter than subsequent advertisements. In some cases, the length of time for an advertisement may be based on the content. Of course, other factors may contribute to the length of time for the advertisements.

In one scenario, auctions may be held periodically for advertisers to place their bids to have video or other ads shown for all content or specific content. Advertisers may place bids for a specific one or more pieces of content, a presented grouping of content, or all available content. The bids may involve placing money in escrow; otherwise payment may be made upon winning the bid. The advertising bids for the content are for enabling advertisements associated with the content for a specified period of time or a specified number of views or plays. After the time that all the bids are due from the advertisers, the winning bid for each piece of content goes to the highest dollar amount bidder and the highest bidders will then be able to show their ad during the specified period of time (or for the specified number of views or plays).

In some cases, there could be a situation where there is a tie in an amount placed as a bid for a particular piece of content. This scenario may occur where bids are submitted blind (e.g., there is no knowledge of other bids) or where bid amounts are not updated as fast as they are submitted. An additional period of time may be provided for those advertisers to bid until a highest bidder is achieved (or the additional time period ends). It is also contemplated that a winning bid could be selected in some other manner that may not be based on the bid being the highest.

In some implementations, an advertiser may select when (e.g., time of day, day of week, after/before a particular location in content), how (e.g., type of advertisement—video, still image, interactive advertisement; how often), and who (e.g., type and/or location of user based on a log-in information of the user or based on internet protocol (IP) address of user) receives the advertisement.

In some implementations, a user may be logged-in while accessing the system and searching and/or reading educational content. In some implementations, cookies may be stored at the user's device so that when the user returns to the website providing the user interface to the educational search and ranking engine, the system can recognize that the user has been on the site before and may even recognize that the user has "opened" some content. A history log or other record may be maintained so that the user can see what content has been reviewed and may more easily return to already viewed content. In some cases, the farthest location and/or bookmarks may be stored for the user so the user may return to a location within content.

The described search and ranking engine may be accessible via a personal assistant such as Ski® available from Apple Inc., Google Now™, or Cortana® available from Microsoft Corp. Queries may be input through voice commands or by touch or text or other input.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A computer-based educational content search and results generation system, the system comprising: one or more non-transitory computer readable storage media having processor executable instructions stored thereon; an educational content database or table stored on the one or more non-transitory computer readable storage media; and an educational content search and ranking engine that, when executed by one or more processors, directs the one or more processors to: provide a graphical user interface that displays a search bar; receive a search query for educational content; perform a search for educational content constrained by the search query; identify a plurality of educational content from the educational content database in response to the search query; identify a number of times each single educational content of the plurality of educational content has been referenced by sources of a set of at least one designated source; transmit a search result of the plurality of educational content that is ordered based on the number of times each single educational content has been referenced; display on the graphical user interface a search result of the plurality of educational content that is in a ranked order based on the number of times each single educational content has been referenced, wherein each respective single ranked educational content of the plurality of ranked educational content has corresponding to it at least one respective source indicator for each respective source that referenced the respective educational content, wherein at least one source indicator comprises a name of the respective source; and display on the graphical user interface a plurality of within educational content ranked previews;

wherein either a single source only contributes a maximum of one source indicator for a respective single ranked educational content, even if a single source has multiple references for the single ranked educational content in a specific filtered time frame, or wherein the single source contributes an unlimited number of source indicators for a respective single ranked educational content; and wherein a plurality of source indicators are horizontal to a highest ranked educational content, and a plurality of source indicators are horizontal to a second highest ranked educational content.

2. The system of claim 1, wherein transmitting a search result of the plurality of educational content comprises transmitting a search result of a plurality of educational content wherein at least one single educational content of the plurality of educational content is a book, video, or article; wherein the set of at least one designated source comprises a set designated by a user; wherein each respective source indicator comprises a name of the respective source; and wherein the set of at least one designated source comprises at least one school, college, university, library, teacher, or professor.

3. The system of claim 2, wherein receiving the search query comprises receiving a term; and wherein each source indicator is linked to a popup that displays information of the respective source.

4. The system of claim 3, wherein receiving the search query comprises receiving a hypertext transfer protocol (HTTP) request for a webpage; wherein providing a graphical user interface that displays a search bar comprises providing a graphical user interface that displays a search bar distinct from at least one drop down menu wherein the at least one drop down menu provides filtering by subject, filtering by time, or filtering by school; and wherein the set of at least one designated source comprises a set designated by a user.

5. The system of claim 4, wherein a search term is altered by the educational content search and ranking engine; and wherein the graphical user interface displays at least two search bars, one for educational content searching and one for within educational content searching.

6. A computer-based educational content search and results generation system, the system comprising: one or more non-transitory computer readable storage media having processor executable instructions stored thereon; an educational content database or table stored on the one or more non-transitory computer readable storage media; and an educational content search and ranking engine that, when executed by one or more processors, directs the one or more processors to: provide a graphical user interface that displays a search bar; receive a search query for educational content; perform a search for educational content constrained by the search query; identify a plurality of educational content from the educational content database in response to the search query; identify a number of times each single educational content of the plurality of educational content has been referenced by sources of a set of at least one designated source; transmit a search result of the plurality of educational content that is ordered based on the number of times each single educational content has been referenced; and display on the graphical user interface a search result of the plurality of educational content that is in a ranked order based on the number of times each single educational content has been referenced, wherein each respective single ranked educational content of the plurality of ranked educational content has corresponding to it at least one respective source indicator for each respective source that referenced the respective educational content; wherein at least one source indicator comprises a name of the respective source; wherein the set of at least one designated source comprises at least one school, university, teacher, professor, library, or educational institution;

wherein the graphical user interface displays at least one within educational content preview;

wherein either a single source only contributes a maximum of one source indicator for a respective single ranked educational content, even if a single source has multiple references for the respective single educational content in a specific filtered time frame, or wherein the single source contributes an unlimited number of source indicators for a respective single ranked educational content;

wherein a plurality of source indicators are horizontal to a highest ranked educational content, and a plurality of source indicators are horizontal to a second highest ranked educational content; and wherein receiving the search query comprises receiving a term.

7. The system of claim 1, wherein the set of at least one designated source comprises at least one school, teacher, professor, primary school, secondary school, trade school, tertiary school, or library; wherein a single source can only contribute a maximum of one source indicator to a respective single ranked educational content; and wherein providing a graphical user interface comprises providing a graphical user interface that displays a search bar distinct from at least one drop down menu, and wherein the at least one drop down menu comprises a plurality of filter parameters.

8. The system of claim 1, wherein identifying the plurality of educational content comprises searching a database of educational content organized by degree, source name, course title, instructor name, department title, and book or other educational content title; wherein identifying the plurality of educational content comprises using the term to search the educational content database by titles of the educational contents and by class and also comprises identifying educational content referenced for classes having a matching class name to the term and identifying educational content having a matching educational content title to the term; and wherein a single source can only contribute a maximum of one source indicator to a respective single ranked educational content.

9. The system of claim 3, wherein how the educational content is referenced affects the search result of the plurality of educational content or the ranked order of the plurality of ranked educational content; and wherein a single source can only contribute a maximum of one source indicator to a respective single ranked educational content.

10. The system of claim 1, wherein receiving the search query comprises receiving a term; wherein identifying the plurality of educational content comprises using the term to search the educational content database for educational content with at least one related search term; wherein a single source can only contribute a maximum of one source indicator for a respective single ranked educational content, even if a single source has multiple references for the respective single educational content in a specific filtered time frame; wherein each source indicator is linked to a popup that displays information of the respective source; wherein the set of at least one designated source comprises at least one school, college, university, teacher, library, or professor; and wherein transmitting a search result of the plurality of educational content that is ordered based on the number of times each single educational content has been referenced comprises transmitting a search result of a plurality of educational content wherein at least one educational content of the plurality of educational content is a book, article, or video.

11. The system of claim 10, wherein receiving the search query comprises receiving a hypertext transfer protocol (HTTP) request for a webpage; wherein providing a graphical user interface that displays a search bar comprises providing a graphical user interface that displays a search bar distinct from at least one drop down menu wherein the at least one drop down menu provides filtering by subject, filtering by time, or filtering by school; and wherein the set of at least one designated source comprises a set designated by a user.

12. The system of claim 11, wherein providing a graphical user interface comprises providing a graphical user interface that displays a plurality of within content ranked previews, and wherein the graphical user interface displays clip segment indicators or locator icons.

13. The system of claim 1, wherein transmitting the search result of the plurality of educational content comprises: ordering the search result with most referenced educational content first and breaking any ties by at least one tie-breaker from the group consisting of: key word matches to educational content title; key word matches to class name; average ranking by at least one ranking organization for the sources that reference the educational content; and alphabetical order by educational content title; and wherein either a single source can only contribute a maximum of one source indicator, for a respective single ranked educational content, even if a single source has multiple references for the respective single educational content in a specific filtered time frame, or wherein a single source can contribute an unlimited amount of source indicators, for a respective single ranked educational content; and wherein the set of at least one designated source comprises a set designated by a user.

14. The system of claim 12, wherein the one or more processors are further directed to:
provide access to the educational content.

15. The system of claim 14, wherein providing access to the educational content comprises: presenting text, images, audio, or video of the educational content; and presenting one or more advertisements at designated times or according to an amount of educational content consumed by the user; and wherein a single source can only contribute a maximum of one source indicator to a respective single ranked educational content.

16. A computer-based educational content search and results generation system, the system comprising: one or more non-transitory computer readable storage media having processor executable instructions stored thereon; an educational content database or table stored on the one or more non-transitory computer readable storage media; and an educational content search and ranking engine that, when executed by one or more processors, directs the one or more processors to: provide a graphical user interface that displays a search bar; receive a search query for educational content; perform a search for educational content constrained by the search query; identify a plurality of educational content from the educational content database in response to the search query; identify a number of times each single educational content of the plurality of educational content has been referenced by sources of a set of at least one designated source; transmit a search result of the plurality of educational content that is ordered based on the number of times each single educational content has been referenced; and display on the graphical user interface a search result of the plurality of educational content that is in a ranked order based on the number of times each single educational content has been referenced, wherein each respective single ranked educational content of the plurality of ranked educational content has corresponding to it at least one respective source indicator for each respective source that referenced the respective single educational content; wherein at least one source indicator comprises a name of the respective source; wherein each source indicator is linked to a popup that displays information of the respective source;
wherein either a single source only contributes a maximum of one source indicator for a respective single ranked educational content, even if a single source has multiple references for the respective single educational content in a specific filtered time frame, or wherein the single source contributes an unlimited number of source indicators for a respective single ranked educational content;
wherein a plurality of source indicators are horizontal to a highest ranked educational content, and a plurality of source indicators are horizontal to a second highest ranked educational content;
wherein how the educational content is referenced affects the search result of the plurality of educational content or the ranked order of the plurality of ranked educational content;
wherein receiving the search query comprises receiving a term; and
wherein identifying the plurality of educational content comprises using the term to search the educational content database by titles of the educational contents and by class names, and also comprises identifying educational content referenced for classes having a matching class name to the term and identifying educational content having a matching educational content title to the term.

17. The system of claim 16, wherein the set of at least one designated source comprises at least one school, teacher, professor, primary school, secondary school, trade school, tertiary school, or library; and wherein either a single source can only contribute a maximum of one source indicator, for a respective single ranked educational content, even if a single source has multiple references for the respective single educational content in a specific filtered time frame, or wherein a single source can contribute an unlimited amount of source indicators, for a respective single ranked educational content; and wherein the set of at least one designated source comprises a set designated by a user.

18. The system of claim 16, wherein identifying the plurality of educational content comprises searching the educational content database, which comprises educational content organized by degree, source name, course title, instructor name, department title, and educational content title; and wherein a single source can only contribute a maximum of one source indicator, for a respective single ranked educational content, even if a single source has multiple references for the respective single educational content in a specific filtered time frame, or wherein a single source can contribute an unlimited amount of source indicators, for a respective single ranked educational content; and wherein the set of at least one designated source comprises a set designated by a user.

19. The system of claim 16, wherein identifying the number of times each educational content of the plurality of educational content has been referenced comprises: identifying the number of times each educational content of the plurality of educational content has been required, recommended, made optional, made supplemental, suggested, mentioned, or assigned, by each source, school, professor, teacher, course, department, degree, or any combination thereof; and wherein a single source can contribute a maximum of one source indicator to a respective single ranked educational content; and wherein the set of at least one designated source comprises a set designated by a user.

20. The system of claim 16, wherein transmitting the search result of the plurality of educational content comprises: ordering the search result with most referenced educational content first and breaking any ties by at least one tie-breaker from the group consisting of: key word matches to educational content title; key word matches to class name; average ranking by at least one ranking organization for the sources that reference the educational content; and alphabetical order by content title; and wherein a single source can only contribute a maximum of one source indicator to a respective single ranked educational content; wherein the set of at least one designated source comprises a set designated by a user; and wherein at least one drop down menu provides for filtering by subject, filtering by time, or filtering by school.

* * * * *